(12) United States Patent
Fymat et al.

(10) Patent No.: US 8,214,023 B2
(45) Date of Patent: Jul. 3, 2012

(54) MICROCIRCULATION IMAGING

(75) Inventors: Alain L. Fymat, Rancho Mirage, CA (US); Max Harry Weil, Rancho Mirage, CA (US); Wanchun Tang, Palm Desert, CA (US); Joe Bisera, Camarillo, CA (US); Giuseppe Ristagno, Palm Springs, CA (US)

(73) Assignee: Institute of Critical Care Medicine, Rancho Mirage, CA (US)

( * ) Notice: Subject to any disclaimer, the term of this patent is extended or adjusted under 35 U.S.C. 154(b) by 1483 days.

(21) Appl. No.: 11/524,866

(22) Filed: Sep. 21, 2006

(65) Prior Publication Data

US 2008/0086057 A1   Apr. 10, 2008

(51) Int. Cl.
*A61B 6/00* (2006.01)
(52) U.S. Cl. ........ 600/473; 600/407; 600/476; 600/477; 600/479; 250/341.1; 250/341.3; 250/341.8
(58) Field of Classification Search .................. 600/310, 600/322, 476, 479, 504, 407, 473, 477; 250/341.1, 250/341.3, 341.8
See application file for complete search history.

(56) References Cited

U.S. PATENT DOCUMENTS

| | | | | |
|---|---|---|---|---|
| 5,262,646 | A * | 11/1993 | Booker et al. | 250/341.4 |
| 5,847,394 | A * | 12/1998 | Alfano et al. | 250/341.8 |
| 5,954,658 | A * | 9/1999 | Gorti | 600/504 |
| 6,104,939 | A * | 8/2000 | Groner et al. | 600/322 |
| 6,577,394 | B1 * | 6/2003 | Zavislan | 356/369 |
| 6,889,075 | B2 * | 5/2005 | Marchitto et al. | 600/473 |
| 2002/0111546 | A1 * | 8/2002 | Cook et al. | 600/322 |

OTHER PUBLICATIONS

Sankaran et al., "Comparative study of polarized light propagation in biologic tissues," Jul. 2002, Journal of Biomedical Optics, 7(3), pp. 300-306.*
Sankaran, et al., "Comparative study of polarized light propagation in biologic tissues" Journal of Biomedical Optics 7(3), 300-306 (Jul. 2002).*
H. Wayland and P.C. Johnson, "Erythrocyte Velocity Measurements in Microvessels by a Two-Slit Photometric Method", Journal of Applied Physiology, vol. 22, pp. 333-337, 1967.
A. L. Fymat, "Jones's Matrix Representation of Optical Instruments: I. Bean Splitters", Applied Optics, vol. 10, No. 11, pp. 2499-2505, Nov. 1971.
A. L. Fymat, "Polarization Effects in Fourier Spectroscopy: I. Coherency Matrix Representation", Applied Optics, vol. 11, No. 1, pp. 160-173, Jan. 1972.

(Continued)

*Primary Examiner* — Brian Casler
*Assistant Examiner* — Daniel Huntley
(74) *Attorney, Agent, or Firm* — Leon D. Rosen

(57) ABSTRACT

An image is created of blood circulation deep (e.g. a plurality of millimeters) below the surface of living tissue to aid in evaluating a patient. A first beam (26) of circularly polarized light is directed forwardly (F) against an outer surface (14) of the tissue. Light that has penetrated to only a shallow depth before moving rearwardly and out of the tissue remains polarized and is blocked by a filter (38). Light that has penetrated to greater depths (12), is scattered more and becomes depolarized, and a portion of it passes through the depolarizing filter (38) and is focused on a photodetector (48) to create an image. Light spots (54) on the image that move, represent spaces between blood platelets (52) that are moving through a capillary, and indicates the velocity of blood through the capillary.

7 Claims, 2 Drawing Sheets

OTHER PUBLICATIONS

F. C. MacKintosh, J. xX. Zhu, D. J. Weitz, "Polarization Memory of Multiply Scattered Light", Physical review, vol. 40, No. 11, pp. 9342-9345, Nov. 1, 1989.

C. G. Ellis, M. L. Ellsworth, R.N. Pittman, and W.L. Burgess, "Application of Image Analysis for Evaluation of Red Blood Cell Dynamics in Capillaries", Microvascular Research, vol. 44, pp. 214-225, 1992.

A. R. Pries, T. W. Secomb, T. Gessner, M.B. Sperandio, J.F. Gross, and P. Gaehtgens, "Resistance to Blood Flow in Microvessels in vivo", Circulation Research, vol. 75, pp. 904-915, 1994.

A. Parthasarathi, S. Japee, and R. Pittman, "Determination of Red Blood Cell Velocity by Video Shuttering and Image Analysis", Annals of Biomedical Engineering, vol. 27, pp. 313-325, 1999.

W. Groner, J.W. Winkelman, A.G. Harris, C. Ince, G. J. Bouma, K. Messmer, and R. Nadeau, "Orthogonal Polarization Spectral Imaging: A New Method for Study of the Microcirculation", Nature Medicine, vol. 5, No. 10, pp. 1209-1213, Oct. 1999.

A. S. De Vriese, T. J. Verbeuren, M. O. Vallez, N. H. Lameire, M. De Buyzere, and P.M. Vanhoutte, "Off-Line Analysis of Red Blood Cell Velocity in Renal Arterioles", Journal of Vascular Research, vol. 37, pp. 26-31, 2000.

J. Lindert, J. Werner, M. Redlin, H. Kuppe, H. Habazettl, A. R. Pries, "OPS Imaging of Human Microcirculation: A short Technical Report", Journal of Vascular Research, vol. 39, pp. 368-372, Apr. 2002.

\* cited by examiner

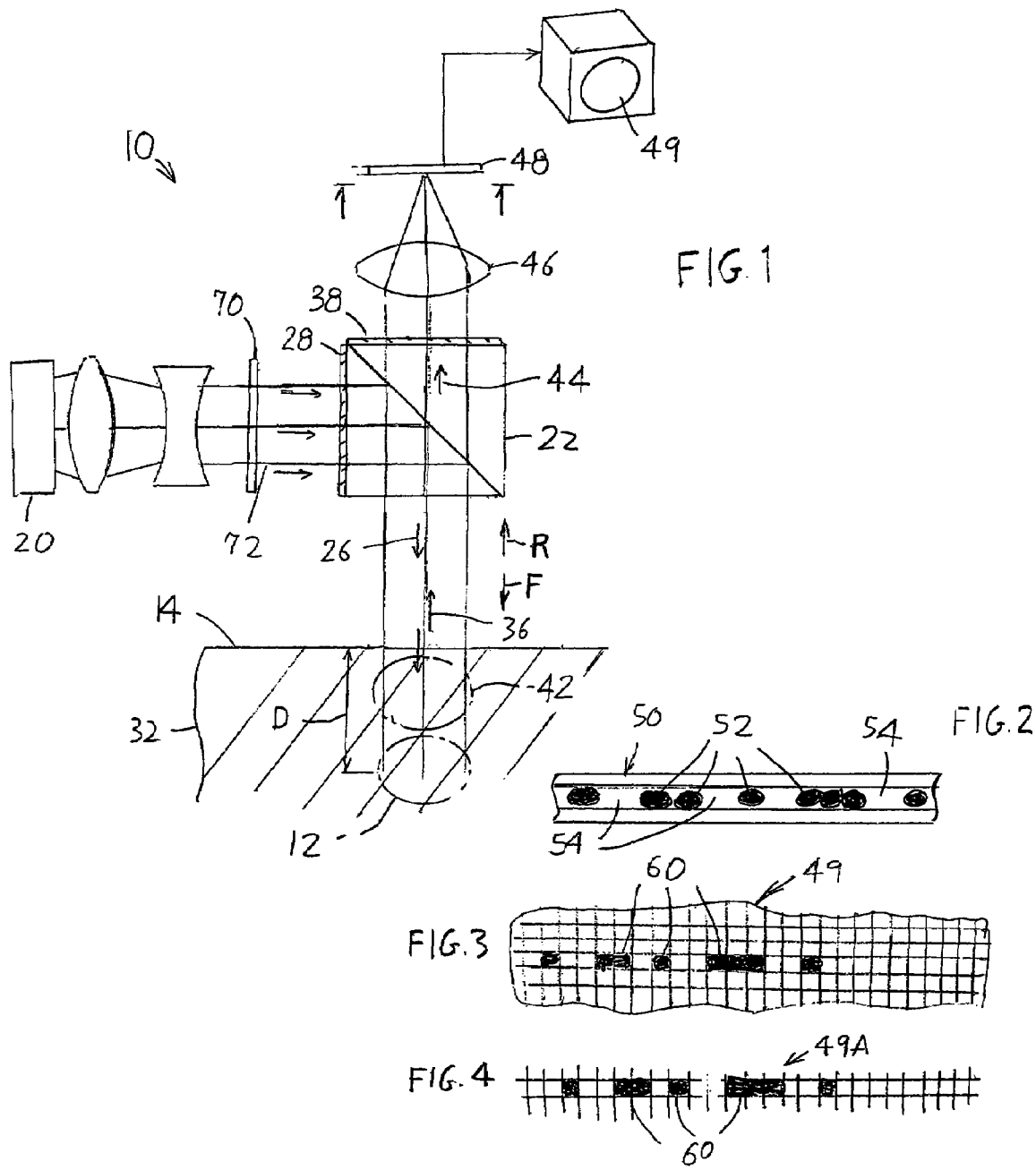

MICROCIRCULATION IMAGING

BACKGROUND OF THE INVENTION

There is a great need to determine whether or not there is sufficient perfusion, or blood circulation, in microvessels of a patient. Such microvessels include capillaries, arterioles and venules, which are herein all referred to as capillaries. Adequate microcirculation is vital for the transport of oxygen and other nutrients and the removal of waste. Distinctive microvascular pathologies are associated with different disease states such as in diabetes, hypertension, chronic heart disease, chronic ulcers and sepsis. One promising noninvasive technique is the shining of bright light at tissue and the detection of reflected and scattered light. However, it is found that this technique indicates microcirculation only at shallow depths of no more than about one millimeter below the tissue surface. It is known that circularly polarized light penetrates further into tissue than linearly or unpolarized light, but this has not led to better interrogation of tissue. There is a need for the noninvasive detection of microcirculation at greater depths of a plurality of millimeters, in order to interrogate deeper tissue layers, especially the surface regions of organs. A noninvasive technique that enabled such deeper detection of microcirculation would be of value.

SUMMARY OF THE INVENTION

In accordance with one embodiment of the present invention, applicant provides a method and apparatus for use in sensing microcirculation at a depth of a plurality of millimeters below the surface of living tissue. A first beam of circularly polarized light is directed forwardly at an outer surface of the tissue to be interrogated. The light penetrates the tissue and is absorbed by and scattered from the tissue. Much scattering occurs when light reaches a boundary between materials of different indexes of refraction. Some of the light passes deeply into the tissue to reach a depth of a plurality of millimeters, and some of such deep light (light which has reached a large depth of a plurality of millimeters) is scattered in a rearward direction.

Some of the deep light which has been scattered travels rearwardly towards the tissue outer surface from a large depth. Such deep light is further scattered by the tissue, and is largely depolarized as it passes rearwardly to constitute a second beam that moves rearwardly out of and then away from the tissue. Light moving out of the tissue along the second beam is filtered to allow only unpolarized light to move along a filtered portion of the second beam. This allows the passage, through the filter, of a higher portion of deep light that has passed rearwardly though the tissue from a large depth. The unpolarized light of the filtered second beam is imaged onto a photodetector such as one with a matrix of photodetecting pixels. The output of the photodetector is used to generate a display which is an image that is largely of tissue at a depth of a plurality of millimeters below the surface of the tissue. The image changes with time and displays moving bright objects which represent spaces between blood platelets moving in one or more capillaries. The rate of such movements represent the velocity of blood in a capillary.

It is known that circularly polarized light penetrates living tissue to a greater depth than unpolarized or linearly polarized light. Thus, a considerable portion of the original circularly polarized light penetrates deeply (a plurality of millimeters) into the tissue and some of this deep light then moves rearwardly and reaches the outer surface of the tissue. Much of such deep light passes through a depolarizing filter that passes only depolarized light to become part of the image on the photodetector and therefore on the display. Such light from deep in the tissue, has undergone many scatterings, and in doing so it has become largely depolarized. As a result, a considerable portion of such light passes through the depolarizing filter that passes only unpolarized light. Some of the light in the rearwardly moving second beam is nondeep light that has penetrated only a small depth of the tissue, that has been scattered much less than the deep light, and that therefore contains a higher portion of polarized light that is blocked by the depolarizing filter. Thus, a considerable portion of the unpolarized light reaching the photodetector is from deep in the tissue and therefore represents microcirculation at a depth of a plurality of millimeters below the tissue surface.

The tissue can be interrogated by directing a wide circularly polarized first beam at the tissue, wherein the first beam converges at the desired depth such as a plurality of millimeters within the tissue. Such beam also is blocked from moving in a direct forward direction into the tissue. As a result, the largely forward-moving first beam illuminates only a deep portion of the tissue. All of the scattered light that moves directly rearwardly though the tissue and out of its surface along a second beam is therefore light that originated from the deep tissue. A result is that more of the unpolarized light that emerges from the tissue along the second beam is light that represents a deep portion of the tissue.

The novel features of the invention are set forth with particularity in the appended claims. The invention will be best understood from the following description when read in conjunction with the accompanying drawings.

BRIEF DESCRIPTION OF THE DRAWINGS

FIG. 1 is a side elevation view of a system for interrogating patient tissue that lies a plurality of millimeters below the tissue surface in order to evaluate blood microcirculation therein.

FIG. 2 is an enlarged view of a capillary of a patient, showing what the system of FIG. 1 can detect.

FIG. 3 is a view of a portion of an image on a display screen of the system of FIG. 1.

FIG. 4 is a view similar to that of FIG. 3 but at a slightly later time.

DESCRIPTION OF THE PREFERRED EMBODIMENTS

Figure 5:
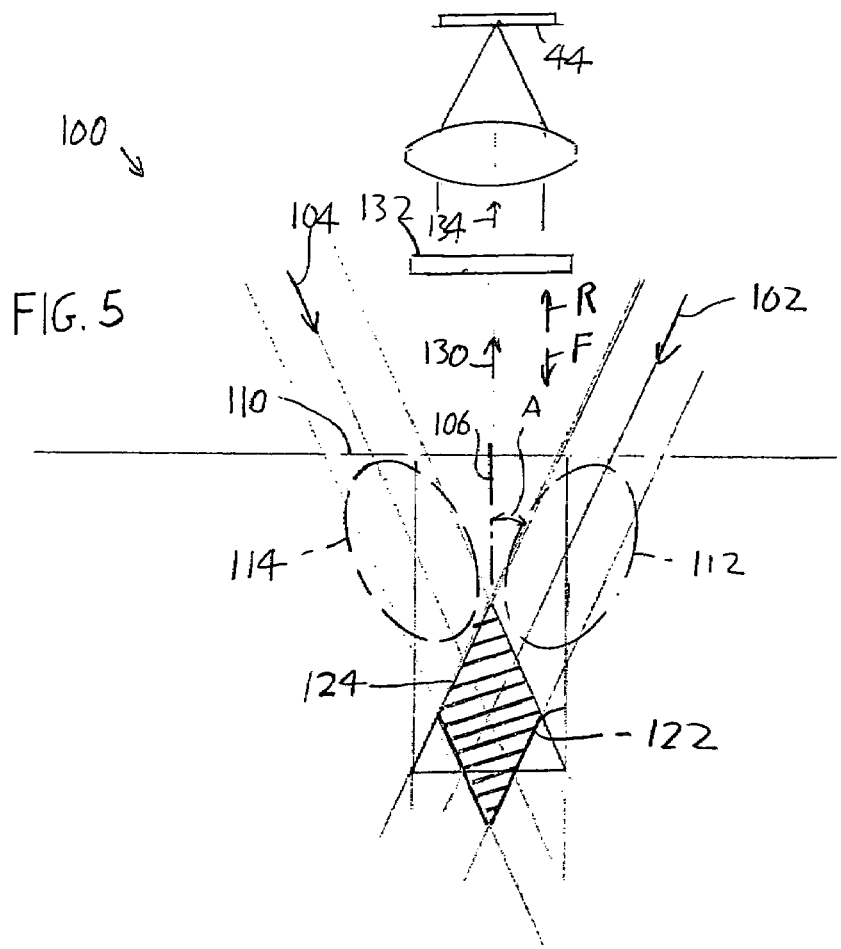
FIG. 5 is a side elevation view of a system similar to that of FIG. 1, but which uses converging beam portions to better interrogate the tissue.

FIG. 1 shows a system 10 for indicating microcirculation in a region 12 that lies deeply (a plurality of millimeters) below an outer surface 14 of tissue of a patient. The system includes a source 20 of light that is directed though a circular polarizer 28. The circular polarizer 28 passes only light that is circularly polarized in a first direction, such as a clockwise direction when the beam is viewed facing along the direction of beam movement. The circularly polarized light passes through a beam splitter 22 that directs the light forwardly F as a first light beam 26 into the surface, or outer surface 14, of living tissue 32 Because of the fact that light in the first beam as it approaches the tissue is circularly polarized, a considerable portion of it reaches the deep region 12 of the tissue, which lies a distance D of a plurality of millimeters below the surface. The beam width is on the order of three millimeters, both along the first light beam 26 and the second light beam at 36 and at 44.

Microvessels, including capillaries, arterioles, and venules, all of which are referred to herein as capillaries, lie in living tissue. The flow, or perfusion, of blood though capillaries lying a plurality of millimeters below the surface of a patient's tissue, such as in the deep region 12, is an important indicator of the patient's condition. The present invention provides a system for indicating microperfusion in such deep regions.

The circularly polarized light that has reached the deep region 12 has been scattered (reflected and refracted) at least about 10 times, and as a result becomes depolarized. Some of that light moves rearwardly R from the deep region and forms part of a second beam 36 that moves rearwardly though the tissue and out of the tissue. As the second beam moves rearwardly through the tissue it also picks up light from a shallow portion 42 of the tissue that lies less than a plurality of millimeters below the tissue surface. Much of this shallow light has been scattered only a few times and is not depolarized. As a result, only a small portion of this light is unpolarized.

FIG. 1 shows that light moving rearwardly along the second beam encounters a depolarizing filter 38 that rejects circularly polarized light and passes primarily only unpolarized light. As mentioned above, the depolarization of deep light results in a greater percent of it being depolarized than shallow light. The unpolarized portion of the second beam becomes an unpolarized second beam portion 44. The unpolarized second beam portion passes through a converging lens 46 that focuses the beam onto a photodetector 48 that usually includes an array of photosensitive pixels, such as a linear array or, more commonly a two-dimensional array. The output of the photodetector is used to create an image on a display screen 49.

Applicant notes that the circular polarizer 28 and the depolarizing filter 38 should be maintained with their faces precisely perpendicular to each other. Applicant assure this by mounting each of them on a corresponding face of the glass beam splitter formed by a pair of prisms with a pair of contacting faces.

FIG. 2 shows a capillary 50, and shows blood platelets 52 and hemoglobin 54 that are passing though the capillary. The blood platelets 52 create dark images at 60 on the display screen 49 of FIG. 3. FIG. 4 shows the display 49A a short time (e.g. a half second) later, showing that the dark images 60 have moved. The fact that the dark images, each of the expected size of a blood platelet, have moved indicates that the image represents blood flow in a capillary. The distance on the screen that the images have moved in a given time period indicates the velocity of blood flow.

As shown in FIG. 1, the light source 20 is collimated and passes though a tuneable spectral filter 70. The light source 20 generates light of a wide range of wavelengths, such as white light. The tuneable spectral filter 70 passes only a limited range of light wavelengths. The collimated beam 72 passes through the beam splitter 22, which directs about half of the light forwardly to become the first beam 26 that moves in the forward direction F into the tissue. The tunable spectral filter allows different wavelengths of light to pass and become part of the first and second beams. For example, light of a range from 420 nanometers (blue-purple light) to 810 nanometers (red to near infrared) may be emitted from the light source. The filter may be tuned to different frequency bands such as to pass only a band from 525 to 575 nanometers (light green) and later a band of 550 to 600 nanometers to see which band produces the clearest image of blood platelets. Applicant notes that oxy-hemoglobin is maximally absorbed at about 420 nanometers (blue purple) while deoxyhemoglobin exhibits multiple scatters in deeper regions at 810 nanometers (red to infrared). A compromise is green light at about 548 nanometers (a majority of light between 500 nanometers and 600 nanometers). The wavelength directed forwardly into the tissue can be a wavelength that is tuned to the absorption bands of a particular blood component, such as oxygen, nitrous dioxide and/or nitrous oxide. A majority of light in the directed beam has a wavelength that is absorbed by blood platelets more than any other frequency, and a wavelength band of 525 to 575 nanometers is preferred.

FIG. 5 illustrates another system 100 wherein a pair of light beams 102, 104 are directed at angles A of 30° to a line 106 that is perpendicular to the tissue surface 110. The light beams pass though tissue regions 112, 114 and illuminate a lower portion of a cylindrical volume 122 of the tissue, with a highest level of illumination being in a deep volume 124 of the tissue. Intense light reaching the volume 124 is largely depolarized and some of it moves rearward along the cylindrical volume 122 to create a second light beam 130 that is large depolarized light. The second light beam passes through a depolarizing filter 132 to create an unpolarized second beam 134 that is imaged onto a photodetector such as 44 in FIG. 1 and the resulting image is displayed. The advantage of the system 100 is that more of the light of the second beam 130 originates from the deep volume 124 of tissue that is to be analyzed, and less of the light originates from more shallow regions below the tissue surface. Also, light directed at the surface of the tissue is diffused over a larger area so more light can be directed at the region 124 of interest without damage to the tissue. The light would appear to intensify as it approaches the deep volume, but the light also diffuses as it approaches the deep volume region 124. Light moving 30° to a line perpendicular to the tissue surface must travel 15% further (1/cos 30°=1.15) to reach the deep region. This is a disadvantage, but is more than compensated for by the much higher light intensity in the deep region than in a shallow region rearward of the deep region.

Figure 6:
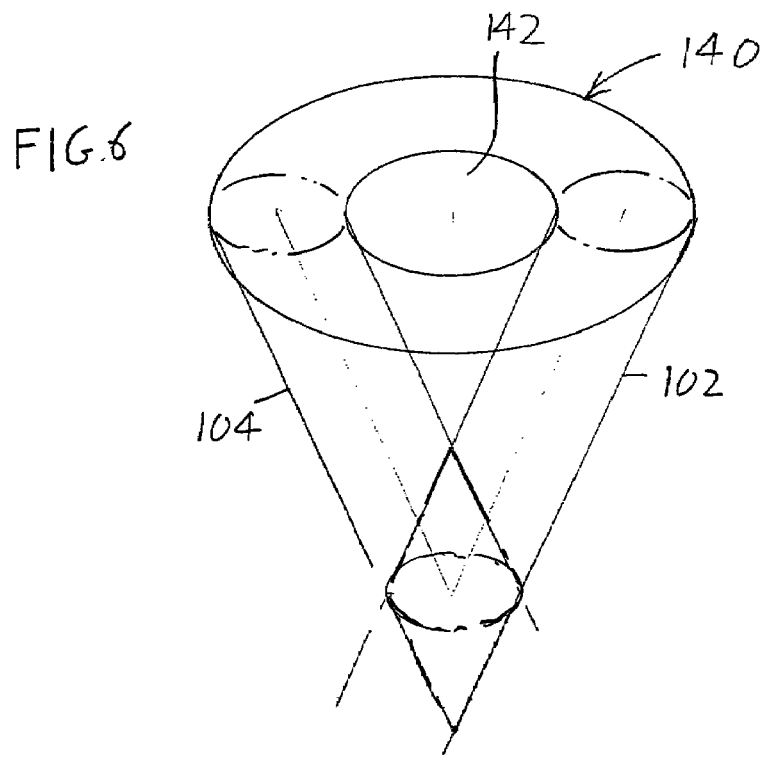
FIG. 6 is an isometric view of a portion of the system of FIG. 5.

FIG. 6 shows that the two beams 102, 104 of FIG. 5 are preferably portions of a conical beam 140 with a conical hole 142 along its axis. The conical beam 140 is readily generated by directing a wider circularly polarized and collimated first beam similar to beam 26 of FIG. 1, through a converging lens, with the middle of the beam blocked.

Thus, the invention provides a method and apparatus for noninvasively interrogating tissue lying more than a minimum distance below the surface of living tissue, such as tissue lying a plurality of millimeters below the tissue surface. This is accomplished by directing circularly polarized light towards the deep tissue, rejecting circularly polarized light that emerges from the deep tissue and detecting only unpolarized light. The detected unpolarized light is focused on a photodetector and the image is displayed. The image can display blood platelets (actually, spaces between platelets) moving though a capillary to help in the diagnosis of a patient. Applicant prefers to direct a beam of a diameter on the order of 3 millimeters at the tissue, or that converges on a deep region of a diameter on the order of 3 millimeters and located a plurality of millimeters forward of the tissue surface such as three millimeters.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A method for use in producing an image of blood that is flowing in capillaries lying within living tissue, comprising:
   directing a first beam of circularly polarized light that is circularly polarized in a predetermined direction, primarily forwardly towards an outer surface of the tissue and allowing the circularly polarized light to penetrate forwardly deep into the tissue and, by light scattering, create a second beam comprising a quantity of light that passes rearwardly through and outside the tissue while illuminating the tissue it passes through and becoming partially unpolarized;
   passing the second beam of partially unpolarized light through a depolarizing filter that blocks all except unpolarized light to produce an unpolarized second beam portion;
   focusing the unpolarized second beam portion onto a photodetector that produces signals representing images of blood particles flowing through capillaries in the tissue.

2. The method described in claim 1 wherein:
   said step of directing a first beam includes directing a pair of beam portions that are each circularly polarized toward said tissue outer surface, and through different regions of said tissue outer surface that are spaced apart at said tissue outer surface to leave a gap between them, so the pair of beam portions do not overlap at a shallow region within the tissue but they overlap deep within the tissue.

3. The method described in claim 1 wherein:
   said step of directing a first beam includes directing primarily light that has a wavelength that is absorbed by blood platelets in a greater percent than the percent absorbed by any other frequencies of light.

4. Apparatus for displaying an image of the flow of blood in capillaries of living tissue, comprising:
   means for directing polarized light primarily forwardly along a first path toward an outer surface of the tissue to pass into the tissue, and for passing rearwardly-moving light that emerges from said tissue outer surface through an optic system that passes primarily only unpolarized light;
   means for focusing the primarily unpolarized light onto a photo detector and for displaying the image that is focused on the photo detector; and
   said means for displaying includes a lens that forms optical images of the actual movement of actual spaces between blood platelets moving in a capillary and of blood platelets that lie between said spaces.

5. The apparatus described in claim 4 wherein:
   said means for directing light forwardly includes means for generating at least two beam portions that converge and that are spaced apart to leave a gap between them at the outer surface of the tissue and that overlap only deep within the tissue.

6. The apparatus described in claim 4 wherein:
   said means for directing light forwardly includes means for directing a cone-shaped beam with a cone-shaped hole in the middle of the beam, toward an outer surface of the tissue, where the cone-shaped beam with a hole converges only within the tissue at a depth of a plurality of millimeters.

7. The apparatus described in claim 4 wherein:
   said means for directing includes a beam splitter formed by a pair of prisms with contacting faces that has a plurality of perpendicular faces, a circular polarizer filter attached facewise to a first of said faces, and a depolarizer filter attached facewise to another of said faces.

* * * * *